(12) United States Patent
Hamamoto

(10) Patent No.: US 7,250,056 B2
(45) Date of Patent: Jul. 31, 2007

(54) LANCET-INTEGRATED MOUNTER AND METHOD OF MAKING THE SAME

(75) Inventor: Katsumi Hamamoto, Otsu (JP)

(73) Assignee: Arkray, Inc., Kyoto (JP)

( * ) Notice: Subject to any disclaimer, the term of this patent is extended or adjusted under 35 U.S.C. 154(b) by 425 days.

(21) Appl. No.: 10/479,528

(22) PCT Filed: Jun. 10, 2002

(86) PCT No.: PCT/JP02/05754

§ 371 (c)(1),
(2), (4) Date: Dec. 1, 2003

(87) PCT Pub. No.: WO02/100272

PCT Pub. Date: Dec. 19, 2002

(65) Prior Publication Data

US 2004/0158271 A1   Aug. 12, 2004

(30) Foreign Application Priority Data

Jun. 11, 2001   (JP)   ............................. 2001-175370

(51) Int. Cl.
*A61B 17/32*   (2006.01)
*A61B 5/151*   (2006.01)

(52) U.S. Cl. .................. 606/181; 600/345; 600/347; 600/365; 600/397

(58) Field of Classification Search .................. None
See application file for complete search history.

(56) References Cited

U.S. PATENT DOCUMENTS

| | | | | |
|---|---|---|---|---|
| 3,665,672 A | * | 5/1972 | Speelman | ................. 53/435 |
| 5,514,152 A | * | 5/1996 | Smith | ................. 606/182 |
| 6,051,392 A | * | 4/2000 | Ikeda et al. | ................. 435/25 |
| 6,264,619 B1 | * | 7/2001 | Ferguson | ................. 600/573 |
| 6,497,845 B1 | * | 12/2002 | Sacherer | ................. 422/104 |
| 2006/0052810 A1 | * | 3/2006 | Freeman et al. | ............. 606/181 |
| 2006/0058827 A1 | * | 3/2006 | Sakata | ................. 606/181 |

FOREIGN PATENT DOCUMENTS

| | | |
|---|---|---|
| JP | 6-38910 | 5/1994 |
| JP | 2616331 | 3/1997 |
| JP | 9-94231 | 4/1997 |
| JP | 2000-231 | 1/2000 |
| JP | 2000-116626 | 4/2000 |
| JP | 2000-116628 | 4/2000 |
| JP | 2000-232973 | 8/2000 |
| JP | 2000-232974 | 8/2000 |

* cited by examiner

*Primary Examiner*—Glenn K. Dawson
(74) *Attorney, Agent, or Firm*—Hamre, Schumann, Mueller & Larosn, P.C.

(57) ABSTRACT

A mounter (3) integrally provided with a lancing element (47B) and analyzer includes a lancing member (47) provided with the lancing element (47B), a first member (4) including an accommodation portion (40) for holding the lancing member (47), and a second member (5) formed separately from the first member (4) for holding the analyzer (6). The accommodation portion (40) includes an accommodation space (43) communicable with the outside through a first opening (43a) and a second opening (43b). The lancing member (47) is held and hermetically sealed in the accommodation space (43) by closing the first opening (43a) and the second opening (43b) with a first seal member (44a) and a second seal member (44b).

21 Claims, 10 Drawing Sheets

LANCET-INTEGRATED MOUNTER AND METHOD OF MAKING THE SAME

TECHNICAL FIELD

The present invention relates to a mounter integrated with a lancet and an analyzer. The invention also relates to a method of making the same.

BACKGROUND ART

For diabetes treatment, management of the blood glucose level by a patient himself or herself is important for maintaining the blood glucose level in a normal range. Particularly, measuring the blood sugar level regularly is essential for a patient of insulin-dependent diabetes to maintain the blood sugar level in a normal range. However, it is troublesome to often go to a medical institution for measuring the blood glucose level. Thus, portable blood glucose level measuring apparatuses are in practical use, which makes it possible to measure the blood glucose level without going to a medical institution.

As an example of such portable blood glucose level measuring apparatuses, the gazette of JP-A-2000-231discloses a concentration measuring apparatus used by attaching a mounter to a main body of a blood glucose measuring apparatus. As shown in FIG. 11 of the present application, the mounter disclosed in the gazette includes a lancing member 70 provided with a lancing needle 70a, and a biosensor 71 retaining enzyme and integrally connected to the lancing member. The lancing needle 70a is accommodated in a space 73 closed by the biosensor 71 as exposed in the space. The biosensor 71 is formed with a through-hole 71a for allowing the movement of the lancing needle 70a. Therefore, in the mounter 7, the lancing needle 70a is exposed whether or not the biosensor 71 is integrally connected to the mounter.

From a hygiene point of view, the lancing needle 70a need be sterilized, and the sterilized state need be maintained until the use of the needle. For this purpose, the lancing needle 70a need be sterilized in a hermetically closed space and the closed state need be maintained until the use. As described above, in the mounter 7, the lancing needle 70a is exposed whether or not the biosensor 71 is integrally connected. Therefore, in the mounter 7, the sterilization of the lancing needle 70a need be performed in the state enclosed by an aluminum laminated film or the like. Therefore, in the mounter 7, the sterilization of the lancing needle 70a cannot be performed in the state separated from the biosensor 71 and hence from enzyme retained in the biosensor 71.

The gazettes of Japanese Patent No. 2616331 and JP-A-9-94231 disclose lancing needles having biosensing function. Japanese Patent No. 2616331 discloses such a biosensor 8 as shown in FIG. 12 of the present application. The biosensor 8 includes a hollow lancing needle (counterpart electrode) 80, and a measurement electrode (operative electrode) 82 which is accommodated in the lancing needle 80 and in which enzyme 81 is fixed. The gazette of JP-A-9-94231 discloses such a biosensing device 9 as shown in FIG. 13 of the present application. The biosensing device 9 includes a lancing needle 90 integrally connected to a capillary 91. In the capillary 91, an operative electrode 92 in which enzyme is fixed, a counterpart electrode 93, and a reference electrode 94 are disposed. Also in the structures disclosed in these gazettes, the sterilization of the lancing needles 80, 90 cannot be performed in the separated state from enzyme.

When the above-described biosensors (biosensing device) are used, the measurement of the blood glucose level is performed using the amperometric method, for example. Specifically, a reaction field is first formed by causing enzyme to coexist with an electron carrier (e.g. potassium ferricyanide). Then, blood is supplied to the reaction field for oxidizing glucose contained in the blood while reducing the electron carrier. Thereafter, voltage is applied to the reaction field to oxidize the electron carrier, and the emitted amount of oxygen is measured as oxidation current. The blood glucose level is computed based on the value of the oxidation current.

The sterilization of the lancing needle may be performed by the radiation of gamma rays, for example. Therefore, when enzyme exists in the sterilizing process of the lancing needle, the enzyme is deactivated or the activity of the enzyme is deteriorated due to the gamma rays radiation. In such a case, a longer time may be required for the measurement or the measured concentration may be lower than the actual concentration, so that proper measurement cannot be performed.

On the other hand, when an electron carrier exists in the sterilizing process of the lancing needle, the electron carrier may be reduced. In such a case, the reaction field includes the reduced electron carrier derived from gamma rays radiation in addition to that derived from enzyme reaction. As described above, in the amperometric method, the blood glucose level is computed based on the amount of electrons emitted from electron carriers. Therefore, when an electron carrier is reduced by gamma rays radiation, the oxidation current value actually measured in applying voltage becomes higher than the value which should be measured. As a result, a concentration value higher than the actual concentration is computed, so that proper measurement cannot be performed.

DISCLOSURE OF THE INVENTION

An object of the present invention is to provide a mounter integrated with a lancet and an analyzer, which is capable of eliminating the disadvantages accompanying the sterilization of the lancet and capable of performing proper concentration measurement.

According to a first aspect of the present invention, there is provided a lancet-integrated mounter comprising a lancing member including a lancing element, a first member including an accommodation portion for holding the lancing member, an analyzer to which body fluid is supplied, and a second member formed separately from the first member for holding the analyzer. The accommodation portion includes an accommodation space communicatable with an outside through a first opening and a second opening, and the lancing member is held in the accommodation space hermetically sealed by closing the first opening and the second opening with a first seal member and a second seal member.

The lancet-integrated mounter may be so structured that the lancing member moves from an idling position to a lancing position upon receiving an external force to cause the lancing element to project from the accommodation portion.

The first seal member is adapted to be formed in exerting the external force to the lancing member, and the lancing element forms a hole in the second seal member in the movement of the lancing member from the idling position to the lancing position. The first seal member and the second seal member may comprise a thin metal film or a resin sheet.

The first member may further include a holder portion for holding the second member, and a support portion for supporting the accommodation portion at a higher position relative to the holder portion. The accommodation portion, the holder portion and the support portion may be integrally formed as one piece by resin molding for example, which is advantageous in terms of the cost. Alternatively, only the accommodation portion may be separately formed. In this case, it is preferable that the accommodation portion is made to be removable from the holder portion and the support portion. With such a structure, in use, the accommodation portion (including the lancing element) can be independently replaced with a new one.

It is preferable that the support portion is elastic. In that case, the support portion may flex to move the accommodation portion downward when an external force in the downward direction is exerted to the accommodation portion and may elastically restore the accommodation portion to an original position when the external force is removed. For making the support portion elastic, the support portion may preferably comprise a plurality of band portions or linear portions.

Preferably, the accommodation portion may be provided with an engagement portion for holding the lancing member at the idling position. The engagement portion may comprise one or a plurality of projections projecting into the accommodation space.

Preferably, the accommodation portion is provided with a stopper for controlling movement of the lancing member at the lancing position. The stopper may be formed by making the diameter of the second opening or the nearby portion smaller than the maximum diameter of the lancing member. More specifically, the stopper may be formed by providing a flange adjacent the second opening to define the diameter of the second opening by the flange or by providing a tapered portion, which reduces the diameter as proceeding toward the second opening, adjacent the second opening.

In the case where the engagement portion and the stopper are provided, it is preferable that the lancing member can be secured between the engagement portion and the stopper. The secured position of the lancing member corresponds to the lancing position.

Preferably, the analyzer may be formed with a cutout for allowing movement of the lancing element. Preferably, the analyzer may be fixed at a position higher than the bottom surface of the second member.

The lancet-integrated mounter is used as incorporated in a concentration measuring apparatus. In this case, the concentration of an object is determined by measuring a current value or voltage value utilizing chemical reaction at the analyzer such as enzyme reaction or by colorimetry. Examples of object to be measured utilizing enzyme reaction include glucose, cholesterol or lactic acid.

According to a second aspect of the present invention, there is provided a method of making a lancet-integrated mounter, the method comprising the steps of forming a lancing member having a lancing element, forming an analyzer to which body fluid is introduced, forming a first member including an accommodation portion having an accommodation space, the accommodation space being communicatable with an outside through a first opening and a second opening, forming a second member separately from the first member, setting the analyzer to be held by the second member, setting the lancing member to be held in the accommodation space, sealing the first opening and the second opening with a first seal member and a second seal member for enclosing the lancing member in the accommodation space, sterilizing the lancing member together with the first member after the sealing step, and fitting the second member holding the analyzer to the first member after the sterilizing step.

Preferably, in the sealing step, the first seal member and the second seal member are attached to the accommodation portion by ultrasonic welding. Preferably, a thin metal film or a resin sheet may be used for making the first seal member and the second seal member.

A typical example of analyzer may be a biosensor retaining oxidoreductase.

The sterilizing step may be performed by irradiating the first member with gamma rays or electron rays.

BEST MODE FOR CARRYING OUT THE INVENTION

An embodiment of the present invention will be described, taking measurement of glucose concentration in blood as an example.

As shown in FIGS. 1 through 4, a blood glucose level measuring apparatus 1 performs lancing operation and blood glucose level measurement in a state where a mounter 3 is mounted to a main apparatus body 2.

Figure 2:
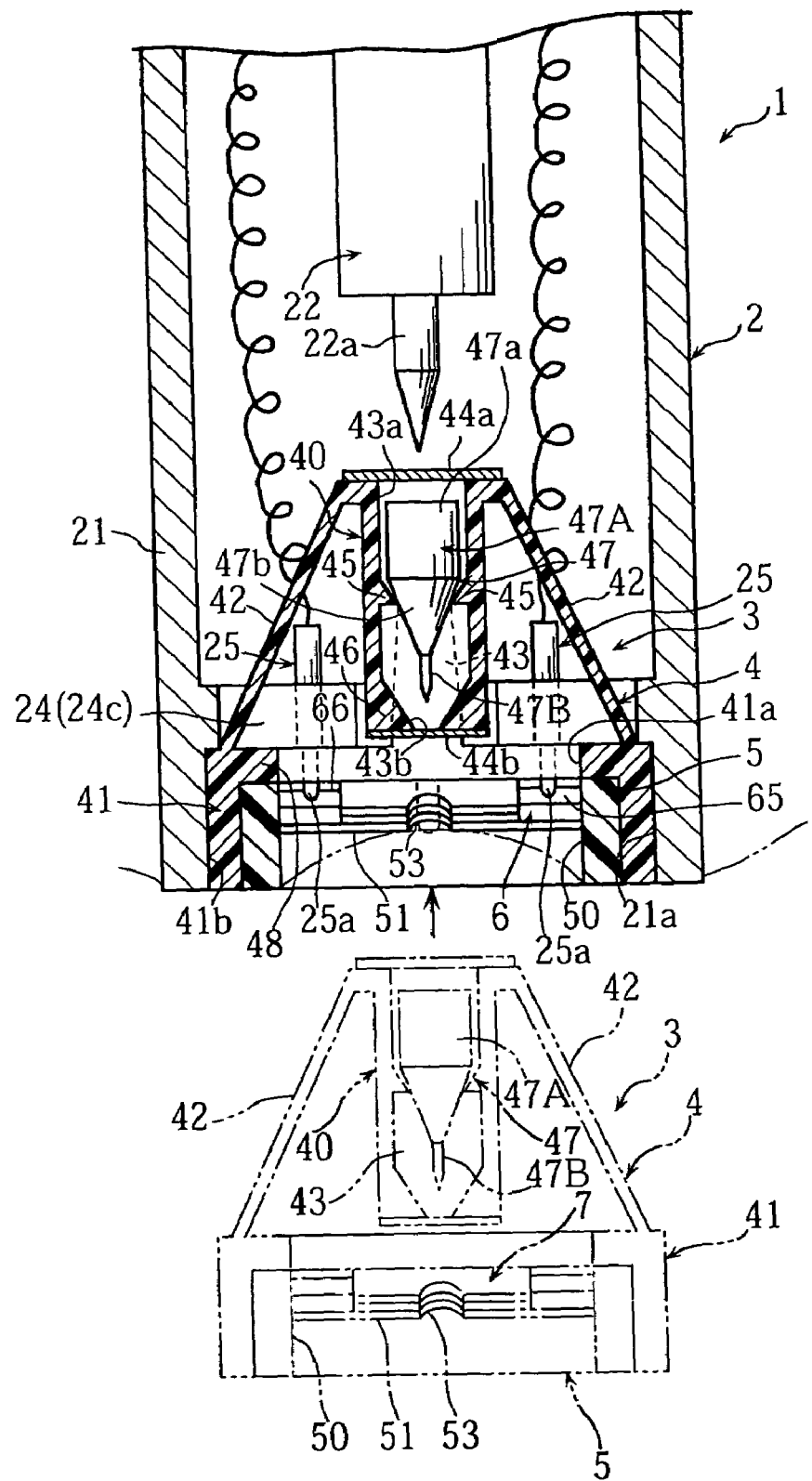
FIG. 2 is a sectional view taken along lines II-II in FIG. 1.
Figure 3:
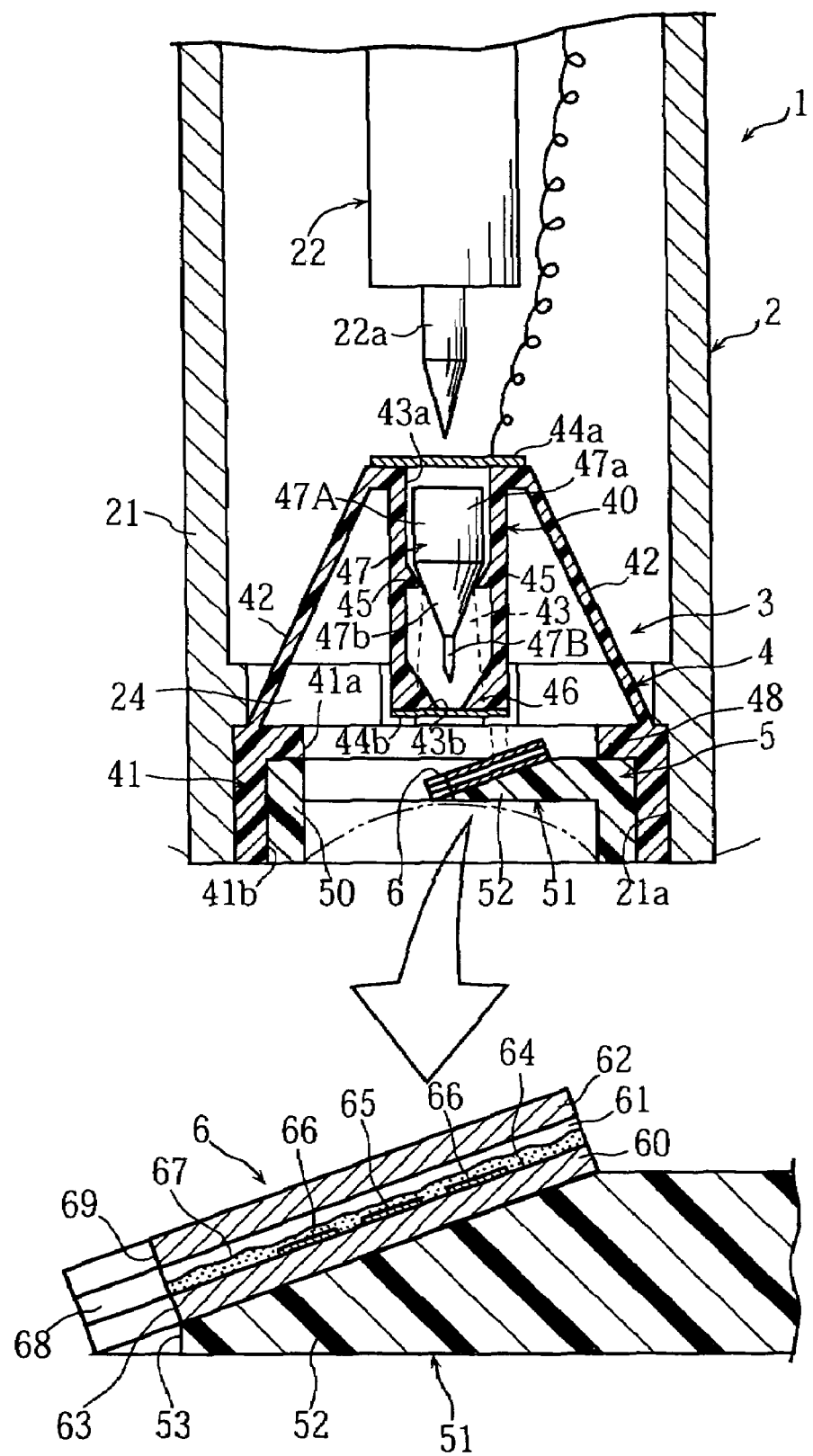
FIG. 3 is a sectional view taken along lines III-III in FIG. 1 and an enlarged view illustrating the principal portion thereof.

As shown in FIGS. 2 and 3, the mounter 3 includes a first member 4, and a second member 5 fitted and held in the first member 4. The first member 4 includes an accommodation portion 40, a holder portion 41 and a plurality of band portions 42.

The accommodation portion 40 includes an accommodation space 43. The accommodation space 43 can communicate with the outside through a first opening 43a and a second opening 43b. The first opening 43a and the second opening 43b are closed with a first and a second seal members 44a and 44b, respectively.

The accommodation space 43 includes a plurality of projections 45 provided therein for serving as engagement portions. The accommodation portion 40 is provided, at a lower position thereof, with a tapered wall 46 serving as a stopper. The tapered wall 46 gradually reduces its diameter as proceeding in the downward direction in FIGS. 2 and 3. Therefore, the second opening 43b is smaller in diameter than the first opening 43a.

In the accommodation space 43, a lancing member 47 is retained in engagement with the plurality of projections 45. The lancing member 47 includes a main body 47A and a lancing needle 47B integrally formed on the main body. The lancing needle 47B may be inserted in resin-molding the main body 47A, for example. The main body 47A includes an operative portion 47a having a constant diameter, and a tapered portion 47b which becomes thinner as proceeding toward the tip end thereof.

The diameter of the operative portion 47a is smaller than that of the first opening 43a and larger than that of the second opening 43b. The operative portion 47a is a portion for exerting a pushing force by a push member 22, which will be described later.

Figure 5A:
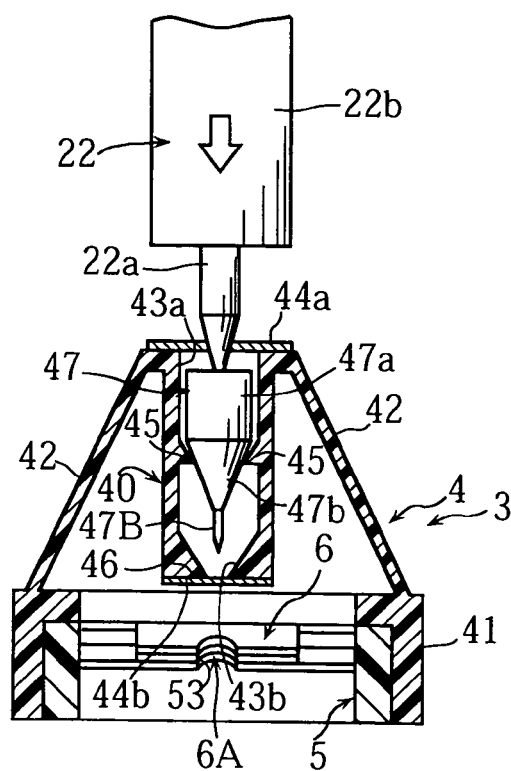
FIGS. 5A through 5D are sectional views of a principal portion for illustrating the lancing operation of the concentration measuring apparatus shown in FIG. 1.
Figure 5B:
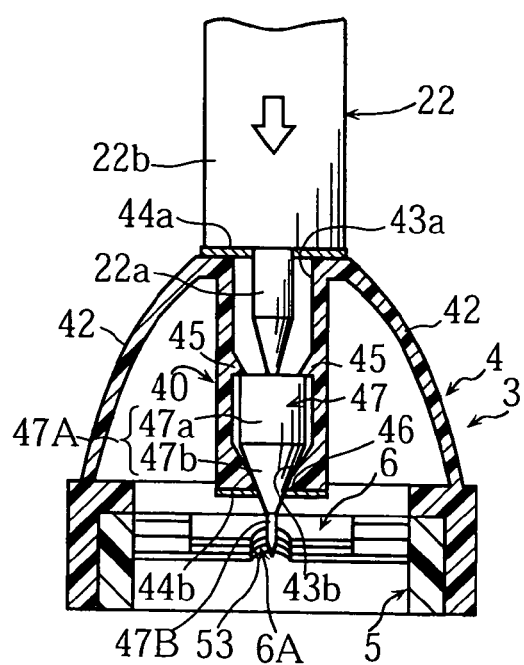

The tapered portion 47b serves to come into engagement with the projections 45. By bringing the tapered portion 47b into engagement with the projections 45, the lancing member 47 can be held at an idling position within the accommodation space 43. In this state, the lancing needle 47b does not project from the accommodation space 43, and the accommodation space 43 is hermetically sealed by the first and the second seal members. On the other hand, when a pushing force is exerted on the operative portion 47a in the downward direction in FIGS. 2 and 3, the tapered portion 47b disengages from the projections 45 so that the lancing member 47 moves downward relative to the accommodation portion 40, as shown in FIGS. 5A and 5B. When the lancing member 47 moves downward a certain distance relative to the accommodation portion 40, the tapered portion 47b interferes with the tapered wall 46 for hindering the movement of the lancing member 47 relative to the accommodation portion 40. The position where the movement of the lancing member 47 is hindered corresponds to the lancing position of the lancing member 47, where the lancing needle 47B projects from the accommodation space 43. When the lancing member 47 is located at the lancing position, the projections 45 engage the upper surface of the operative portion 47a to prevent the rebounding of the lancing member 47. In this way, the projections 45 also serve as a stopper.

The holder portion 41 has a generally cylindrical configuration having a first opening 41a and a second opening 41b. The holder portion 41 is provided, on the upper side in FIGS. 2 and 3, with a flange 48b so that the first opening 41a is smaller in diameter than the second opening 41b. The holder portion 41 functions to hold the second member 5 fitted therein. In fitting the second member 5, the flange 48 interferes with the second member 5, thereby controlling the hold position of the second member 5.

Each of the band portions 42 connects between an upper portion of the accommodation portion 40 and an upper surface of the holder portion 41. (Herein, the term "upper" indicates the upper side in FIGS. 2 and 3). The band portions 42 serve as supports for supporting the accommodation portion 40 relative to the holder portion 41.

Each of the band portions 42 is flexible and functions as a leaf spring. The dimension and material of the band portion 42 is so selected that the band portion has a sufficient strength to support the accommodation portion 40 without flexing in the natural state in which no external force is exerted on the accommodation portion 40.

Figure 5C:
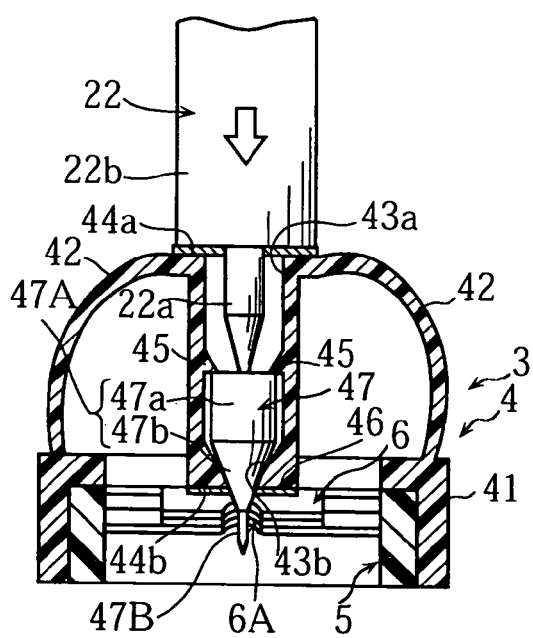
Figure 5D:
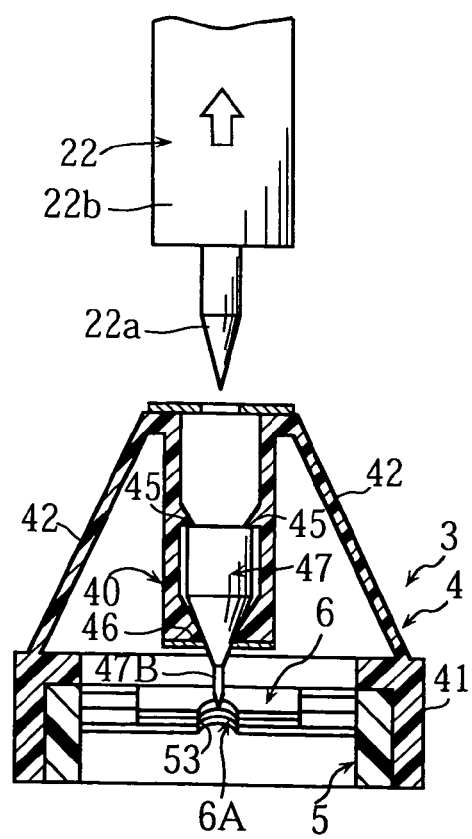

When an external force in the downward direction in FIGS. 2 and 3 is exerted onto the accommodation portion 40, the plurality of supports 42 are flexed as shown in FIGS. 5B and 5C, thereby moving the accommodation portion 40 downward. As shown in FIG. 5D, when the external force to the accommodation portion 40 is removed, the accommodation portion 40 returns to its original position by the elastic restoring force of the supports 42.

The first member 4 having the above-described structure may be formed as one piece by resin molding. Alternatively, the first member 4 may be provided by assembling a plurality of parts formed by resin molding. Each of the supports (42) may comprise a resilient member such as a coil spring or urethane foam. In such a case, the holder portion 41 and the accommodation portion 40 are formed separately from each other, and the supports 42 are connected to these parts. Alternatively, the holder portion 41 and the supports (42) may be integrally formed as one piece, while the accommodation portion 40 may be formed separately. In such a case, it is preferable that the accommodation portion 40 is made as a removable part. In that case, the accommodation portion 40 hermetically sealed while holding the lancing member 47 therein can be detached from the holder portion 41, which is integrally formed with the supports 42, for replacement in use.

Figure 1:
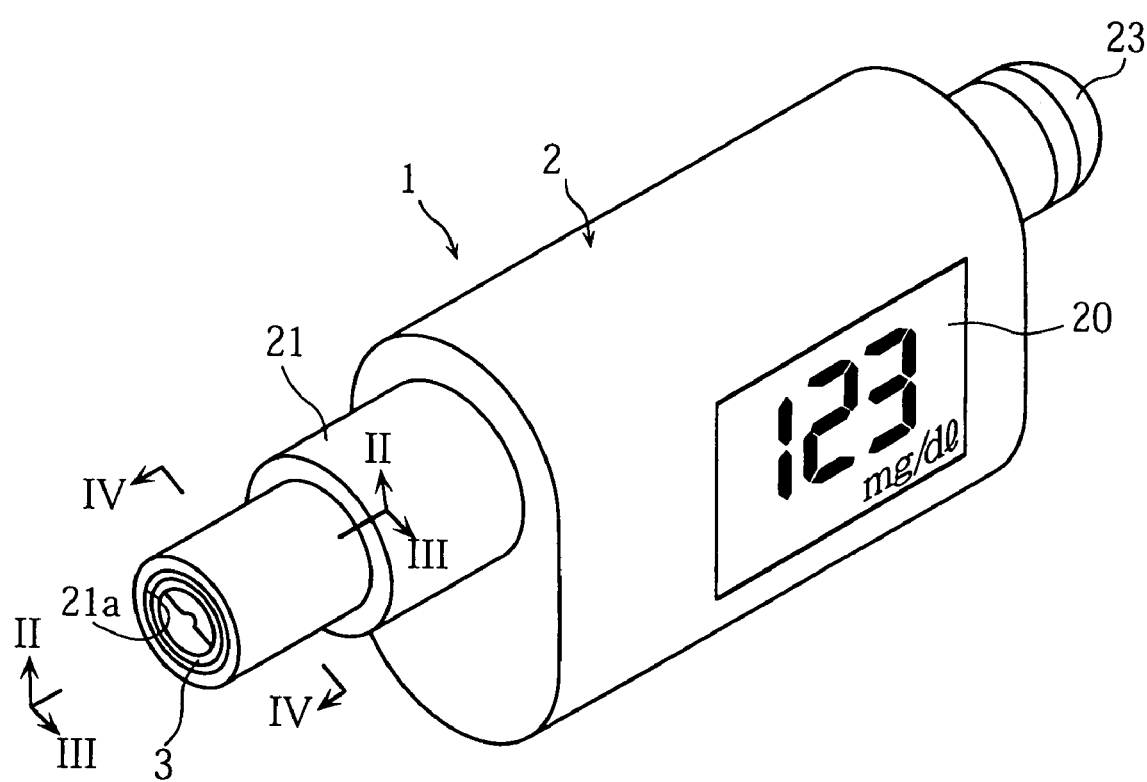
FIG. 1 is a perspective view illustrating the entirety of an example of concentration measuring apparatus to which a mounter according to the present invention is mounted.
Figure 6:
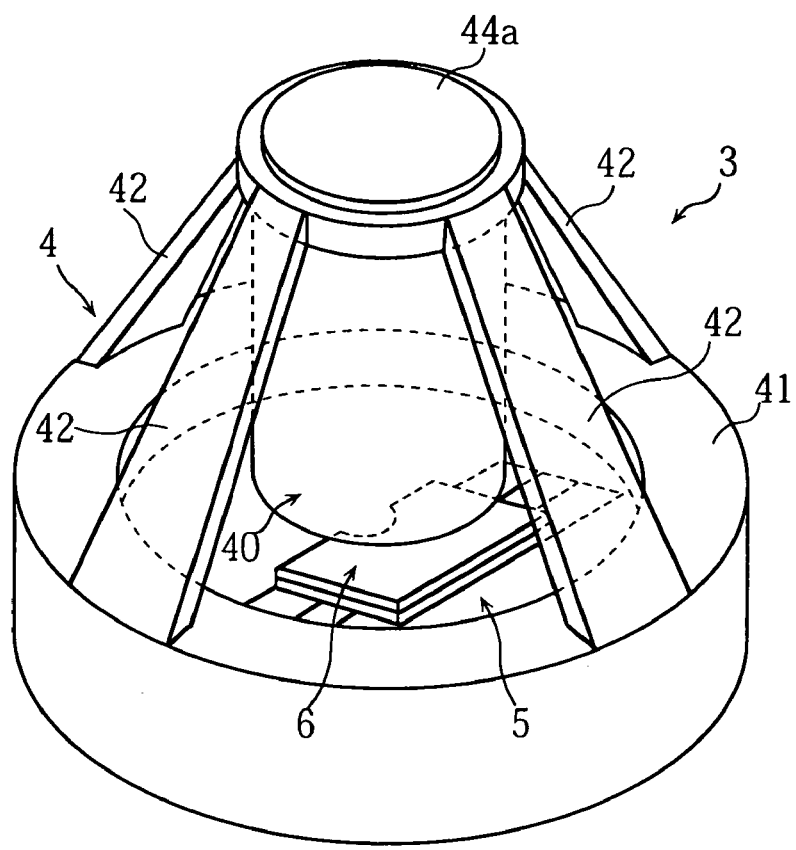
FIG. 6 is a perspective view illustrating the entirety of the mounter according to the present invention.
Figure 7:
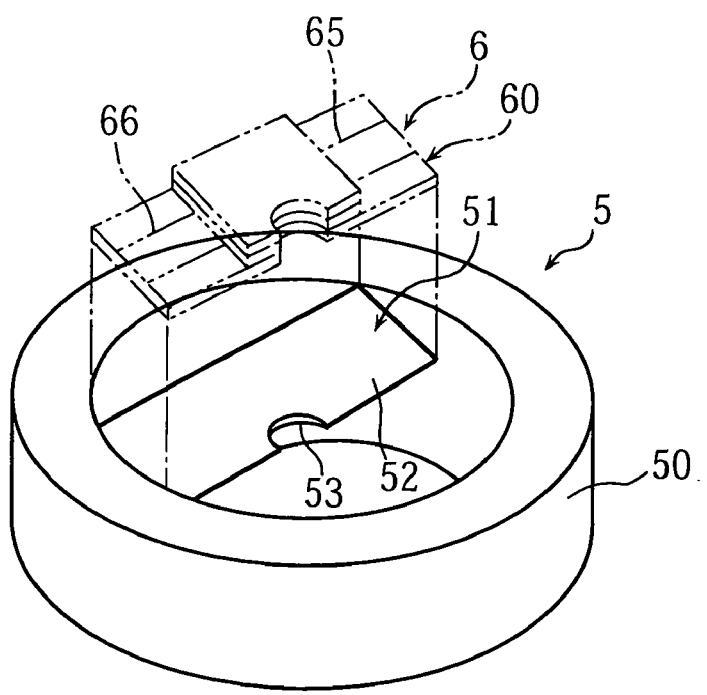
FIG. 7 is a perspective view illustrating the entirety of a second member of the mounter shown in FIG. 6.

As clearly shown in FIG. 7, the second member 5 includes a cylindrical wall 50, and a set portion 51 closing almost half of one opening. The set portion 51 has a tapered portion 52 which becomes thinner as proceeding toward one edge thereof. The edge of the tapered portion 52 is formed, at the middle portion thereof, with a semicircular cutout 53. As shown in FIGS. 1 and 6, a biosensor 6 is placed on the tapered portion 52. Therefore, the biosensor 6 is held as inclined.

The illustrated set portion 51 is provided at a location higher than the bottom surface of the second member 5. In the case where such a structure is employed, it is preferable that when the blood glucose level measuring apparatus 1 is pressed against the skin surface, a negative pressure is generated using a pump for example so that the lancing operation is performed with the skin surface bulged, as shown in FIGS. 2 and 3. In the case where the lancing operation is performed without causing the skin surface to bulge, the set portion 51 is made generally flush with the bottom surface of the second member 5, and the lancing needle 47B projects below the bottom surface of the second member 5.

Figure 8:
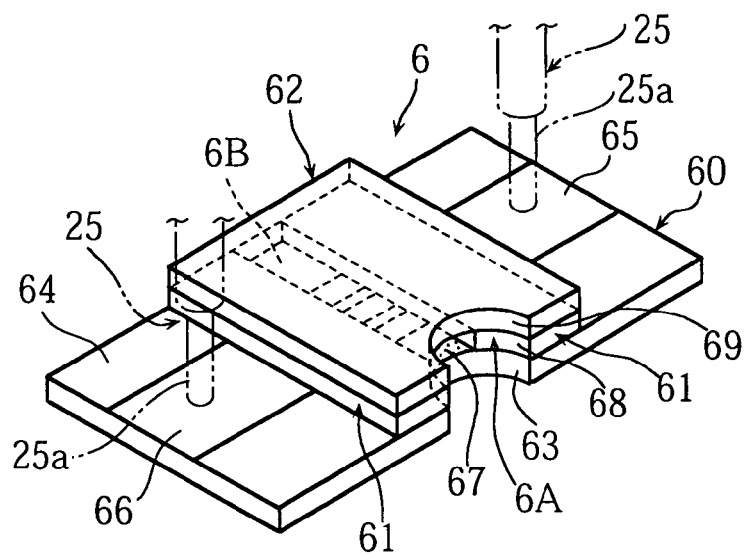
FIG. 8 is a perspective view illustrating the entirety of a biosensor.
Figure 9:
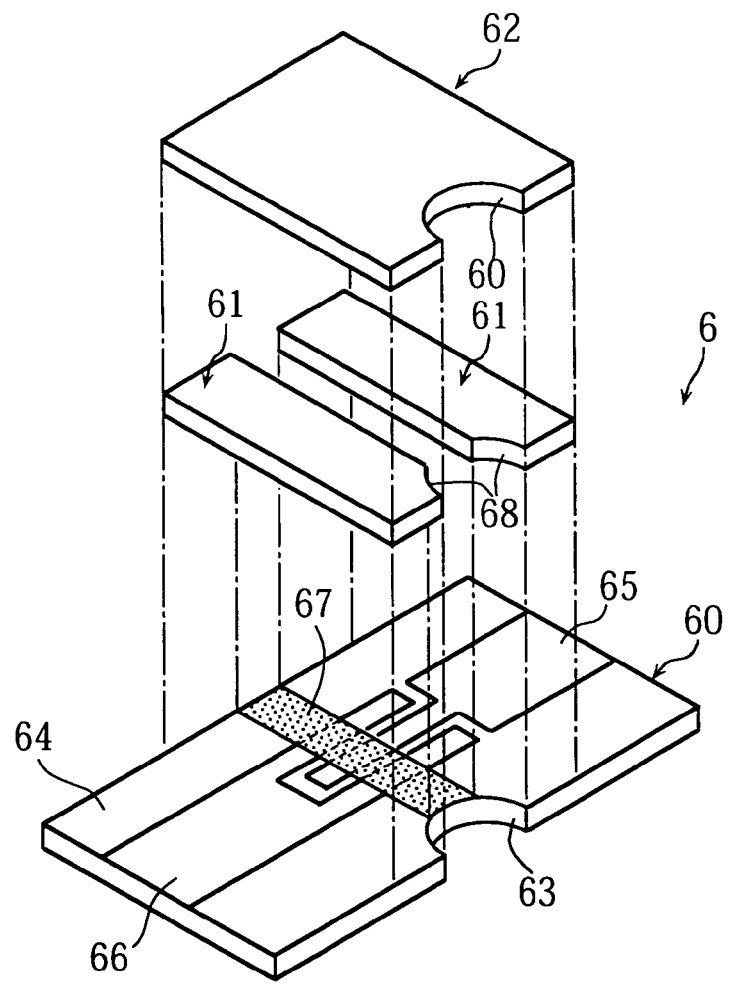
FIG. 9 is an exploded perspective view of the biosensor shown in FIG. 8.

As shown in FIGS. 8 and 9, the biosensor 6 includes a substrate 60, a pair of spacers 61 and a cover 62.

The substrate 60 is made of an insulating material and has an elongated rectangular configuration. The substrate has an opposite pair of longitudinal edges one of which is formed, at the middle portion thereof, with a cutout 63 corresponding to the cutout 53 of the second member 5.

The substrate 60 has a surface 64 formed with an operative electrode 65 and a counterpart electrode 66. The operative electrode 65 extends from one of end edges toward a middle portion of the substrate 60 and includes a narrower portion at the middle portion of the substrate 60. The counterpart electrode 66 extends from the other one of the end edges toward the middle portion of the substrate 60 and is forked at the middle portion of the substrate 60 for sandwiching the operative electrode 65. The operative electrode 65 and the counterpart electrode 66 can be formed by screen-printing carbon ink or forming a conductive film by sputtering or vapor deposition followed by etching.

The surface 64 of the substrate 60 is further formed with a reacting portion 67. The reacting portion 67 is in the form of an elongate strip extending from the cutout 63 to the other longitudinal edge of the substrate across the operative electrode 65 and the counterpart electrode 66. The reacting portion 67 is in a solid state, containing oxidoreductase such as glucose dehydrogenase and an electron carrier such as potassium ferricyanide. Such a reacting portion 67 may be formed by applying slurry containing oxidoreductase and an electron carrier by screen printing or the like followed by drying.

The reaction portion 67 is flanked by the paired spacers 61 arranged in parallel with each other and spaced from each other by a distance corresponding to the width of the reaction portion 67. Each of the spacers 61 has an elongated rectangular configuration having a length corresponding to the width of the substrate 60. Each spacer 61 has one corner portion formed with a cutout 68. The cutout 68 is provided at a location corresponding to the cutout 63 of the substrate 60. The spacer 61 may comprise a double-sided tape or an adhesive, for example.

The cover 62 is so fixed as to bridge the paired spacers. The cover 62 has an opposite pair of end edges one of which is formed with an arcuate cutout 69. The cutout 69 is provided at a location corresponding to the cutout 63 of the substrate 60.

In the biosensor 6, the substrate 60, the spacers 61 and the cover 62 are respectively formed with cutouts 63, 68 and 69. Therefore, the biosensor 6 has a semicolumnar recess 6A extending in the thickness direction and opening in the widthwise direction of the substrate. As shown in FIG. 5, the lancing needle 47B passes through the recess 6A in the lancing operation. Further, as can be inferred from FIGS. 2 and 3, the recess serves as a receiver of blood coming out from the skin.

The biosensor 6 includes a flow path 6B defined by the substrate 60, the spacers 61 and the cover 62 and crossing the substrate 60 in the widthwise direction. The flow path has one end communicating with the outside through the recess 6A and the other end also communicating with the outside. Therefore, when blood is introduced through the recess 6A, the blood travels toward the other end by capillary action. In the flow path 6B is provided the reacting portion 67. Therefore, the reacting portion 67 is dissolved when the blood travels through the flow path 6B. At that time, glucose in the blood is oxidized by enzyme reaction, and the electron carrier is reduced by an electron deriving from the reaction.

The mounter 3 having the above-described structure is made in the manner described below. It is to be noted that the following is based on the assumption that the first and the second members 4 and 5 have been formed in advance by e.g. resin molding, and the lancing member 47 and the biosensor 6 have also been formed in advance.

Figure 10A:
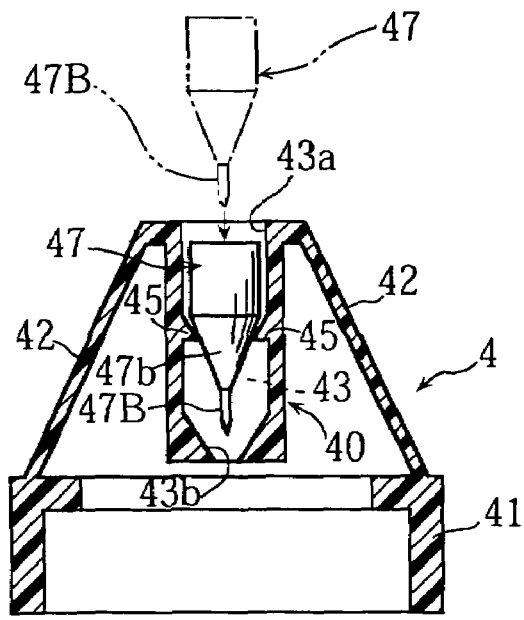
FIGS. 10A through 10D illustrate a method for making the mounter shown in FIG. 6.

Firstly, as shown in FIG. 10A, the lancing member 47 is inserted from the side of the lancing needle 47B through the first opening 43a of the accommodation portion 40. As a result, the tapered portion 47b of the lancing member 47 engages the projections 45 of the accommodation portion 40 so that the lancing member 47 is held in the accommodation space 43.

Figure 10B:
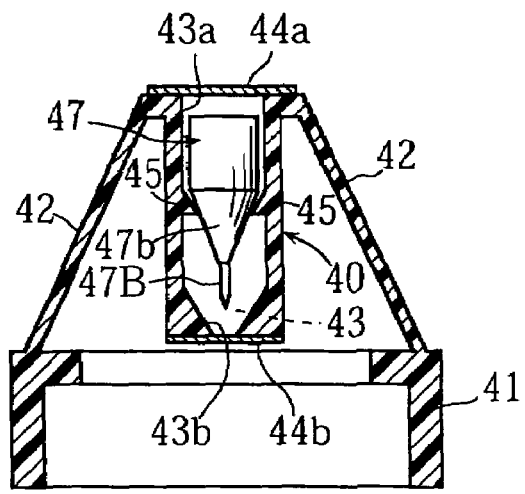

Subsequently, as shown in FIG. 10B, the first and the second openings 43a and 43b of the accommodation portion 40 are closed with the first and the second seal members 44a and 44b. As a result, the lancing member 47 (lancing needle 47B) is accommodated in the hermetically sealed space. The closing of each of the openings 43a, 43b is performed by attaching a thin metal film such as aluminum foil or a resin sheet to the opening by ultrasonic welding. The first member 4 holding the lancing member 47 enclosed therein is sterilized together with the lancing needle 47B. The sterilizing process may be performed by the radiation of gamma rays or electron rays, for example.

Figure 10C:
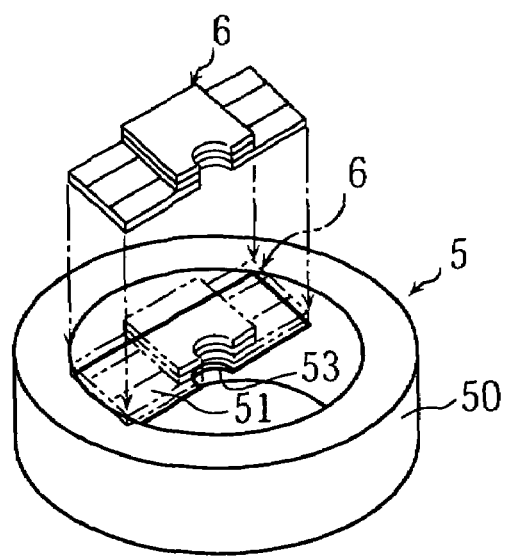

On the other hand, before or after enclosing the lancing member 47, the biosensor 6 is fixed onto the set portion 51 of the second member 5, as shown in FIG. 10C. The fixing of the biosensor 6 may be performed by using a double-sided tape or an adhesive.

Figure 10D:
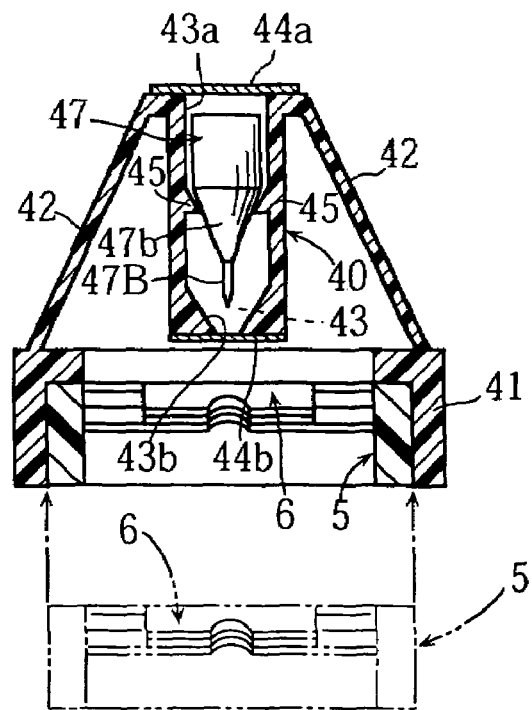
Figure 11:
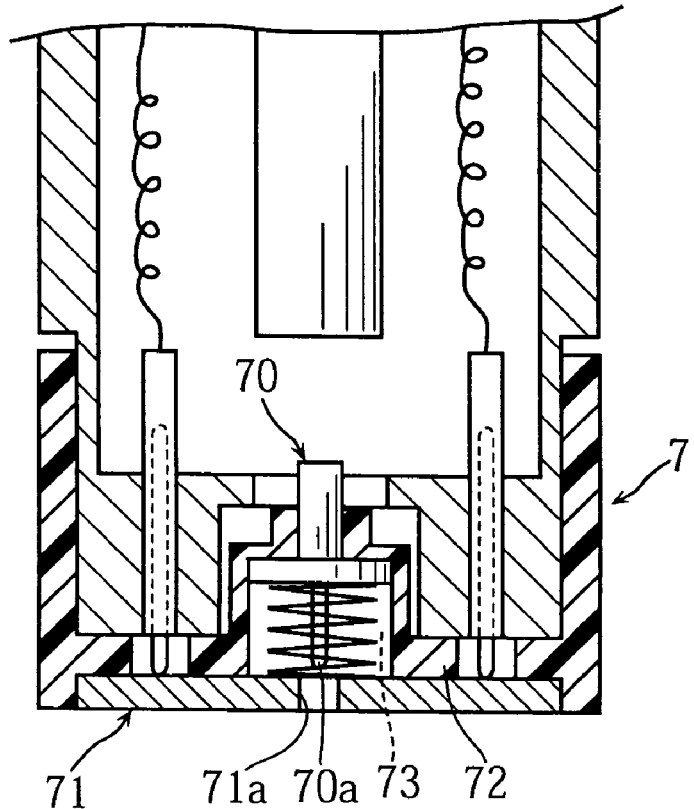
FIG. 11 is a sectional view illustrating a principal portion of a prior-art blood glucose level measuring apparatus.
Figure 12:
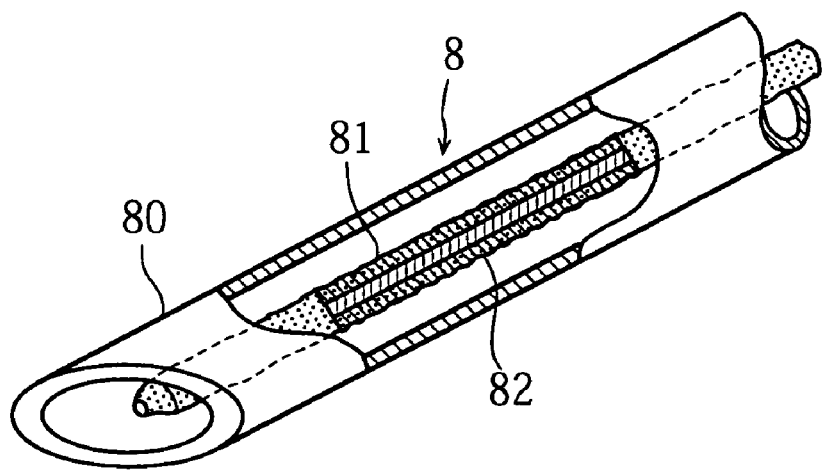
FIG. 12 is a perspective view, which is partially cut away for illustrating a principal portion, of a biosensor having a lancing needle incorporating an enzyme-fixed electrode.
Figure 13:
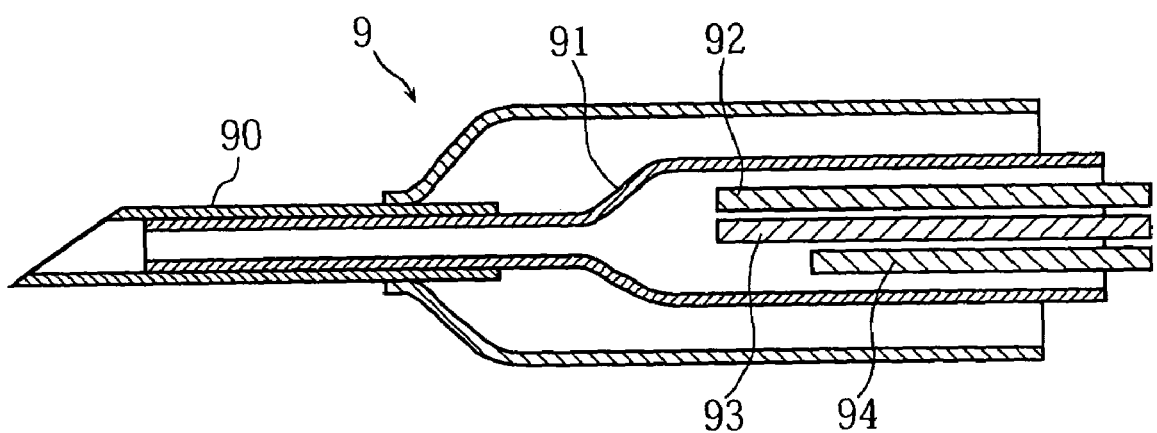
FIG. 13 is a sectional view illustrating a biosensing device in which a lancing needle is integrally formed on a biosensor.

Finally, as shown in FIG. 10D, the second member 5 is fitted into the holder portion 41 of the first member 4, thereby providing a mounter 3.

In the above-described method for making the mounter 3, the sterilization of the lancing needle 47B is performed in a state in which the lancing needle is separated from the biosensor 6. Therefore, the sterilizing process does not cause modification or deactivation of oxidoreductase constituting the reacting portion 67 or reduction of the electron carrier. Therefore, the deterioration of measurement accuracy due to the sterilizing process of the lancing needle 47B can be prevented.

As shown in FIG. 1, the apparatus body 2 is provided with a display 20, and a push button 23. As shown in FIGS. 2 and 3, the apparatus body 2 includes a housing 21 having an end opening 21a. In the end opening 21a of the housing 21 is fitted and retained the mounter 3. The housing 21 holds the push member 22 which is movable between an idling position and a 20 pushing position. The push member 22 comprises a main body 22b, and a needle portion 22a projecting from the main body. By pressing the push button 23, the push member 22 located at the idling position moves to the pushing position.

As means for moving the push member 22, a mechanism may be utilized which latches the push member 22 as biased toward the end opening 21a and releases the latch when the push button 23 is pressed. As means for biasing the push member 22, use may be made of a resilient member such as a coil spring or foamed resin. Alternatively, for moving the push member 22, a magnet may be attached to the push member 22 or to a member which moves together with the push member while an electromagnet is disposed in facing relation to the magnet. With this structure, by pressing the push button 23, a repulsive force is generated between the magnet and the electromagnet, so that the push member 22 is moved to the pushing position.

As shown in FIG. 5A, in the moving process of the push member 22 to the pushing position, the needle portion 22a of the push member 22 pierces a hole in the first seal member 44a and then pushes the operative portion 47a of the lancing member 47. As a result, as shown in FIG. 5B, the lancing member 47 (tapered portion 47b) is disengaged from the projections 45 and moves to the second seal member 44b. In this process, the lancing needle 47B pierces a hole in the second seal member 44b. Finally, the tapered portion 47b of the lancing member 47 interferes with the tapered wall 46 of the accommodation portion 40, so that the lancing member 47 stops its movement relative to the accommodation portion 40. In this state, the lancing needle 47B projects from the second opening 43b.

At the same time, as shown in FIGS. 5B and 5C, the main body 22b of the push member 22 pushes the accommodation portion 40, so that the band portions 42 flex to move the accommodation portion 40 downward. As a result, the tip end of the lancing needle 47B moves below the through-hole 53 of the second member 5. Therefore, when the lancing operation is performed with the housing 21 pressed against the skin surface of a human body, the lancing needle 47B sticks into the skin for causing bleeding (See FIGS. 2 and 3). Since the lancing needle 47B passes through the recess 6A of the biosensor 6 in the lancing operation, the blood from the skin is retained in the recess 6A and then introduced into the flow path 6B (See FIG. 8). On the other hand, as shown in FIG. 5D, the push member 22 elastically returns to the upper side so that the pushing force to the accommodation portion 40 is removed. As a result, the accommodation portion 40 returns to the upper side due to the elastic restoring force of the supports 42.

The lancing operation may be performed by attaching the mounter to a movable member which is movable in the housing and causing the mounter to move together with the movable member. In this case, by the impact in bringing the mounter into contact with the skin surface, a pushing force is exerted to the accommodation portion and hence to the lancing member, thereby causing the lancing member to move (pierce).

Figure 4:
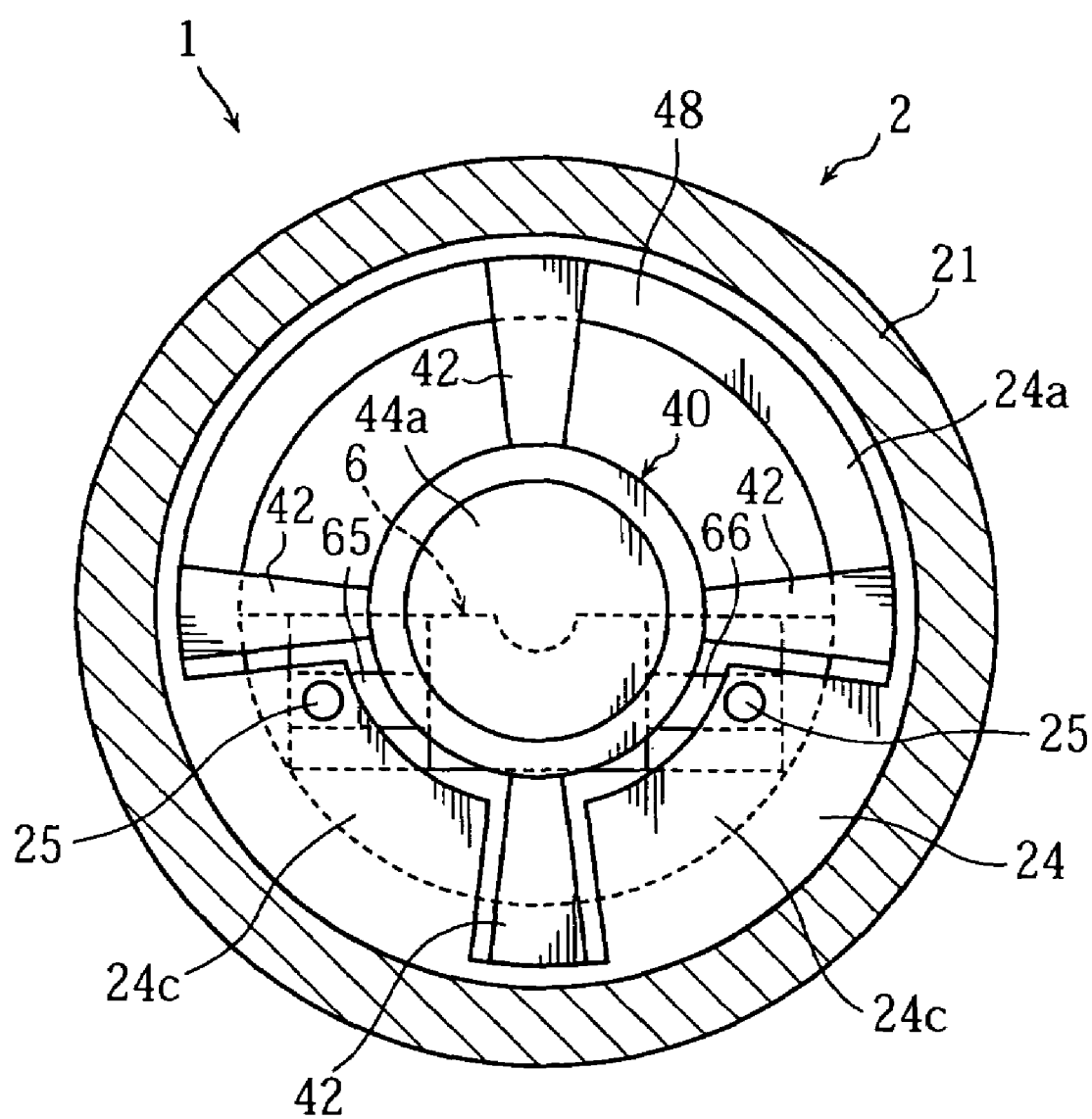
FIG. 4 is a sectional view taken along lines IV-IV in FIG. 1.

As shown in FIGS. 2 and 4, the housing 21 is further provided with a stopper wall 24 projecting from the inner surface of the housing 21. In inserting the mounter 3 into the housing 21, the stopper wall 24 interferes with the holder portion 41 to control the position of the mounter 3. Therefore, as clearly shown in FIG. 4, the stopper wall so configured as not to hinder the insertion of the accommodation portion 40 and the band portions 42. Specifically, the stopper wall 24 includes an arcuate region 24a having a constant width, and two island regions 24c which are separated by a slit 24b and each of which is positioned between adjacent band portions 42 when the mounter 3 is mounted in the housing 21.

As shown in FIGS. 2 and 4, the island regions 24c hold a pair of connectors 25. Each of the connectors 25 includes projects elastically. As shown in FIG. 8, when the mounter 3 is held in the housing 21, the connector pins 25a are brought into contact with the operative electrode 65 and the counterpart electrode 66 of the biosensor 6. The connectors 25 are connected to a non-illustrated electric circuit and hence are capable of applying voltage across the operative electrode 65 and the counterpart electrode 66 and measuring anode current from the operative electrode 65.

At the reacting portion 67 of the biosensor 6, the electron carrier of an oxidation type changes to a reduction type due to the enzyme reaction caused by the supply of blood. Therefore, when voltage is applied across the operative electrode 65 and the counterpart electrode 66 via the connectors 25, the electron carrier changed to the reduction type changes to the oxidation type. This oxidation reaction causes oxidation current to flow through the operative electrode 65. The value of the oxidation current can be measured by utilizing the connectors 25. On the other hand, the electric circuit computes the glucose concentration in the sample liquid based on the oxidation current value and displays the result at the display 20.

Although a concentration measuring apparatus for measuring a blood glucose level is exemplarily described in this embodiment, the technical idea of the present invention is applicable to any other measuring apparatus which performs the lancing operation and the measuring operation simultaneously. For example, the technical idea of the present invention is also applicable to an apparatus for measuring the concentration of cholesterol or lactic acid utilizing enzyme reaction or to an apparatus for measuring concentration by colorimetry.

The invention claimed is:

1. A lancet-integrated mounter comprising: a lancing member including a lancing element and being forwardly movable for lancing, a first member including an accommodation portion for holding the lancing member, an analyzer to which body fluid is supplied, and a second member spaced from the accommodation portion in a forward direction of the lancing member and formed separately from the first member for holding the analyzer;
   the accommodation portion including an accommodation space communicatable with an outside through a first opening and a second opening;
   the lancing member being held and hermetically sealed in the accommodation space by closing the first opening and the second opening with a first seal member and a second seal member, the analyzer being held by the second member outside the sealed accommodation space.

2. The lancet-integrated mounter according to claim 1, wherein the lancing member moves from an idling position to a lancing position upon receiving an external force to cause the lancing element to project from the accommodation portion.

3. The lancet-integrated mounter according to claim 2, wherein the first seal member is adapted to be formed with a hole in exerting the external force to the lancing member, and
   the lancing element forms a hole in the second seal member during the movement of the lancing member from the idling position to the lancing position.

4. The lancet-integrated mounter according to claim 2, wherein the accommodation portion is provided with an engagement portion for holding the lancing member at the idling position.

5. The lancet-integrated mounter according to claim 4, wherein the accommodation portion is provided with a stopper for controlling movement of the lancing member at the lancing position.

6. The lancet-integrated mounter according to claim 5, wherein the lancing member at the lancing position is secured between the engagement portion and the stopper.

7. The lancet-integrated mounter according to claim 1, wherein the first member further includes a holder portion for holding the second member, and a support portion for supporting the accommodation portion at a higher position than the holder portion.

8. The lancet-integrated mounter according to claim 7, wherein the accommodation portion, the holder portion and the support portion are integrally formed as one piece.

9. The lancet-integrated mounter according to claim 7, wherein the accommodation portion is formed separately from the holder portion and the support portion, the accommodation portion being removable from the holder portion and the support portion.

10. The lancet-integrated mounter according to claim 7, wherein the support portion is elastic, and
    the support portion flexes to move the accommodation portion downward when an external force in the downward direction is exerted to the accommodation portion and elastically restores the accommodation portion to an original position when the external force is removed.

11. The lancet-integrated mounter according to claim 10, wherein the support portion comprises a plurality of band portions or linear portions.

12. The lancet-integrated mounter according to claim 1, wherein the analyzer is formed with a cutout for allowing movement of the lancing element.

13. The lancet-integrated mounter according to claim 1, wherein the analyzer is fixed at a position higher than a bottom surface of the second member.

14. The lancet-integrated mounter according to claim 1, wherein the analyzer is a biosensor retaining oxidoreductase.

15. A method of making a lancet-integrated mounter, the method comprising the steps of:

forming a lancing member having a lancing element;

forming an analyzer to which body fluid is introduced;

forming a first member including an accommodation portion having an accommodation space, the accommodation space being communicatable with an outside through a first opening and a second opening;

forming a second member separately from the first member;

setting the analyzer to be held by the second member;

setting the lancing member to be held in the accommodation space;

sealing the first opening and the second opening with a first seal member and a second seal member for enclosing the lancing member in the accommodation space;

sterilizing the lancing member together with the first member after the sealing step; and fitting the second member holding the analyzer to the first member after the sterilizing step.

16. The method of making a lancet-integrated mounter according to claim 15, wherein the sealing step comprises attaching the first seal member and the second seal member to the accommodation portion by ultrasonic welding.

17. The method of making a lancet-integrated mounter according to claim 16, wherein the first seal member and the second seal member comprise a thin metal film or a resin sheet.

18. The method of making a lancet-integrated mounter according to claim 15, wherein the analyzer is a biosensor retaining oxidoreductase.

19. The method of making a lancet-integrated mounter according to claim 15, wherein the sterilizing step is performed by irradiating the first member with gamma rays or electron rays.

20. A lancet-integrated mounter comprising: a lancing member including a lancing element, a first member including an accommodation portion for holding the lancing member, an analyzer to which body fluid is supplied, and a second member formed separately from the first member for holding the analyzer;

the accommodation portion including an accommodation space communicatable with an outside through a first opening and a second opening;

the lancing member being held and hermetically sealed in the accommodation space by closing the first opening and the second opening with a first seal member and a second seal member;

wherein the first member further includes a holder portion for holding the second member, and a support portion for supporting the accommodation portion at a higher position than the holder portion.

21. A lancet-integrated mounter comprising: a lancing member including a lancing element, a first member including an accommodation portion for holding the lancing member, an analyzer to which body fluid is supplied, and a second member formed separately from the first member for holding the analyzer;

the accommodation portion including an accommodation space communicatable with an outside through a first opening and a second opening;

the lancing member being held and hermetically sealed in the accommodation space by closing the first opening and the second opening with a first seal member and a second seal member;

wherein the analyzer is formed with a cutout for allowing movement of the lancing element.

* * * * *